United States Patent [19]

Park

[11] Patent Number: 5,206,141

[45] Date of Patent: Apr. 27, 1993

[54] OKADAIC ACID TESTING FOR CIGUATOXIN

[75] Inventor: Douglas L. Park, Tucson, Ariz.

[73] Assignee: Hawaii Chemtect International, Pasadena, Calif.

[21] Appl. No.: 765,052

[22] Filed: Sep. 24, 1991

[51] Int. Cl.$^5$ .................. C12Q 1/00; G01N 33/53; G01N 33/48; G01N 33/543

[52] U.S. Cl. .................. 435/7.1; 435/810; 422/61; 436/8; 436/63; 436/518; 436/528; 436/531; 436/178

[58] Field of Search .................. 436/8–18, 436/63, 518–535, 178; 422/61; 435/7.1–7.95, 810

[56] References Cited

U.S. PATENT DOCUMENTS

| | | | |
|---|---|---|---|
| 4,703,017 | 10/1987 | Campbell et al. | 436/501 |
| 4,725,553 | 2/1988 | Guadagno | 422/61 |
| 4,816,392 | 3/1989 | Hokama | 435/7 |
| 4,968,604 | 11/1990 | Beatty | 422/56 |

OTHER PUBLICATIONS

Suganuma et al., Proc. Nat'l. Acad. Sci. USA, 85, pp. 1768–1771 (1988).
Hokama et al, Food Agric. Immunol. 1(1), pp. 29–36 (1989) Abstract, Biosis 90:76094.
Hokama et al., "Evaluation of the Stick Enzyme Immunoassay in Caranx sp. and Seriola dumerili Associated with Ciguatera," J. Clin. Lab. Anal., 4, 363–366 (1990).
Singer et al., "The Latex Fixation Test: I. Application to the Serologic Diagnosis of Rheumatoid Arthritis," Am. J. Med., 21, 888–892 (1956).
Hokama et al., "Monoclonal Antibodies in the Detection of Ciguatoxin and Other Toxic Polyethers in Fish Tissues by a Rapid Poke Stick Test," Proceedings of the 5th Int'l. Coral Reef Congress, Tahiti, vol. 4 (1985).
Hokama et al., "A Radioimmunoassay for the Detection of Ciguatoxin," Toxicon, 15, 317–325 (1977).
Hokama et al., "A Rapid Enzyme–Immunoassay for the Detection of Ciguatoxin in Contaminated Fish Tissues," Toxicon, 21, 817–824 (1983).
Hokama, "A Rapid, Simplified Enzyme Immunoassay Stick Test for the Detection of Ciguatoxin and Related Polyethers from Fish Tissues," Toxicon, 23, 939–946 (1985).
Hokama et al., "Assessment of a Rapid Enzyme Immunoassay Stick Test for the Detection of Ciguatoxin and Related Polyether Toxins in Fish Tissues," Biol. Bull., 172, 144–153 (1987).
Hokama, "Ciguatera Fish Poisoning," J. Clin. Lab. Anal., 2, 44–50 (1988).
Hokama et al., "Monoclonal Antibody (MAb) in Detection of Ciguatoxin (CTX) and Related Polyethers by the Stick-Enzyme Immunoassay (S-EIA) in Fish Tissues Associated with Ciguatera Poisoning," 7th Int'l. IUPAC Symposium on Mycotoxins and Phycotoxins, Tokyo, Japan, Aug. 16–19, 1988.
Hokama, "Simplified Solid-Phase Immunobead Assay for Detection of Ciguatoxin and Related Polyethers," J. Clin. Lab. Anal., 4, 213–217 (1990).
McMillan et al., "Ciguatera Fish Poisoning in the United States Virgin Islands: Preliminary Studies," J. Coll. Virgin Islands, 6, 84–107 (1980).
Kimura et al, "Evaluation of the radioimmunoassay (RIA) for detection of Ciguatoxin (CTX) in fish tissues," J. Fish Biol., 21, 671–680 (1982).
Juranovic et al., "Foodborne Toxins of Marine Origin: Ciguatera," Rev. Env. Contam. & Toxicol., 117, 51–94.

Primary Examiner—James C. Housel
Assistant Examiner—N. Bhat
Attorney, Agent, or Firm—Christie, Parker & Hale

[57] ABSTRACT

A composition comprising okadaic acid for use as a positive control in assays for the detection of ciguatoxins and methods for making such compositions. In a preferred embodiment, the okadaic acid composition further comprises a carrier selected from the group consisting of fish extract, oils, oil/organic solvent mixtures, fatty-acid solutions, and non-ionic detergent solutions. A kit for detecting the presence of ciguatoxin or related polyether marine toxins in fish, comprising positive control supports impregnated with a composition comprising okadaic acid.

33 Claims, No Drawings

OKADAIC ACID TESTING FOR CIGUATOXIN

FIELD OF THE INVENTION

The present invention relates to the use of okadaic acid as a positive control and a standard in testing for ciguatoxin-contaminated fish.

BACKGROUND OF THE INVENTION

Ciguatera poisoning is a particular type of fish poisoning which results from the ingestion of contaminated fish. Intoxication is associated with the consumption of toxins produced by the tropical dinoflagellates, including *Gambierdiscus toxicus*, which are subsequently passed along the marine food chain to man. Ciguatoxins are polyether marine toxins, and approximately 27 different ciguatoxins are known, approximately 23 of which are toxic to man. Ciguatera toxins are odorless, tasteless, heat-stable, and generally undetectable by simple chemical tests.

Humans are susceptible to ciguatera poisoning, both from eating toxic herbivores which ingest the dinoflagellates while feeding on red or brown algae, and from eating carnivores which have eaten the toxic herbivores. An accurate assessment of the incidence of ciguatera poisoning is not available; however, it is estimated that, each year, from 10,000 to 50,000 people who live in or visit tropical and subtropical areas suffer from ciguatera poisoning. Additionally, the threat of this contamination results in enormous economic losses in the recreational and commercial exploitation of fishery resources in the affected areas. With increased utilization of tropical reef fish in the continental United States, through interstate commercial trade and tourist travel, incidents of ciguatera poisoning are on the increase.

The onset of the clinical symptoms of ciguatera poisoning occurs within 10 minutes to 24 hours following the consumption of contaminated fish. Ciguatera poisoning affects the digestive system (resulting in abdominal pain, diarrhea, vomiting, nausea); the cardiovascular system (resulting in bradycardia, hypotension, tachycardia); and the neurological system (resulting primarily in paraesthesia and dysesthesia).

Immunological methods have been developed for the identification of ciguatoxin in fish, such as those described in U.S. Pat. No. 4,816,392. These methods offer a relatively simple method of assaying for ciguatoxin. However, such assays incorporate the requirement for "controls." Positive and negative controls are necessary in such assay reactions so that the user of the assay can determine if the reagents are functioning correctly. Also, positive and negative controls provide standard reactions with which the user can compare test assay results to determine if a positive or negative reaction has been obtained. The term "positive control" as used herein means a composition which reacts with antibodies or other assay reagents in a manner similar to ciguatoxin-containing fish extracts to give a positive reaction when assayed. The term "negative control" refers to a sample which contains all the components of a test assay sample, except for a ciguatoxin-containing fish extract or such toxins, and which does not react with antibodies against ciguatoxin, therefore giving a negative reaction when assayed.

Previously, fish extracts have been used as a positive control for ciguatoxin assays. However, such extracts vary in their composition, with respect to the ciguatoxins they contain and the concentration of the ciguatoxin(s) present, and, therefore, also vary in their reactivity. As a result, fish extracts exhibit variable reactivity and give results that are not reproducible. Also, to determine the toxicity of ciguatoxin in fish extracts, toxicity assays, such as assaying the toxicity of the ciguatoxin in mice, have to be performed. Such assays are time-consuming and expensive.

An additional drawback of the use of fish ciguatoxin extracts is that, for mass production of kits for the assaying of fish which may contain ciguatoxin or other "screening" assay methods, enormous numbers of toxic fish would be required for the production of ciguatoxin extract for the positive controls. The requirement for such large amounts of ciguatoxin extracts could make the routine testing of fish impractical or too expensive to be feasible, and results would vary with different fish ciguatoxin extract preparations.

There exists a need, therefore, for a composition which will reliably and reproducibly react in a ciguatoxin assay to mimic the results that would be obtained with a ciguatoxin-contaminated fish and which is readily available and relatively inexpensive.

SUMMARY OF THE INVENTION

The present invention relates to a composition comprising okadaic acid for use as a positive control in assays for the detection of ciguatoxins and methods for making such compositions.

In a preferred embodiment, the okadaic acid composition further comprises a carrier selected from the group consisting of fish extract, oils, oil/organic solvent mixtures, fatty-acid solutions, and non-ionic detergent solutions, wherein: the oil is selected from the group consisting of soybean oil, jojoba oil, olive oil, safflower oil, or mixtures thereof; the organic solvent of the oil-/organic solvent mixture is selected from the group consisting of hexane, butanol, or mixtures thereof; the fatty acid is selected from the group consisting of lauric acid, linoleic acid, myristic acid, palmitic acid, stearic acid, oleic acid, and mixtures thereof; and the non-ionic detergent is selected from the group consisting of the polyoxyethylenesorbitan detergents, and mixtures thereof.

In a preferred embodiment of the present invention, the okadaic acid composition results in a reaction, when assayed, equal to the intensity obtained with assays of about 25 mg/ml toxic fish extract.

The present invention also relates to a kit for detecting the presence of ciguatoxin or related polyether marine toxins in fish, which comprises supports for binding toxin, negative control supports, positive control supports impregnated with a composition comprising okadaic acid, a fixer for fixing toxin to the support, an assay reagent for assaying toxin or okadaic acid bound to the fixed support, and a buffer solution for washing the fixed toxin-bound supports after they have been contacted with the assay reagent.

DETAILED DESCRIPTION

The present invention relates to a composition comprising okadaic acid and a method for using the composition as a positive control in assays for the detection of fish contaminated by ciguatoxin, which is also referred to as toxin. The okadaic acid composition, which mimics assay results obtained with ciguatoxin-contaminated fish, also has uses as a "standard" for use in quantitating the sensitivity and specificity of preparations of antibodies against ciguatoxin or other ciguatoxin assay components. Okadaic acid also has uses in comparing and developing new assay methods to the results obtained with assay procedure that have previously been developed, and in quality control of assay reagents and components that are mass-produced over a period of time.

ANTIBODY CIGUATOXIN ASSAY METHODS

Methods for assaying ciguatoxins in fish, such as that described in U.S. Pat. No. 4,816,392, have used sticks coated with correction fluid to adsorb ciguatoxin from the flesh of contaminated fish. A sample of the ciguatoxin that may be present in the fish is adsorbed onto the correction fluid of the stick by inserting the stick into and contacting it with the flesh of the fish. The ciguatoxin adsorbed onto the correction fluid is then bound to an antibody against ciguatoxin, the antibody having previously been coupled to horseradish peroxidase. The presence of ciguatoxin is determined by assaying for the horseradish peroxidase activity. The term "antibody against ciguatoxin" as used herein means an antibody which binds to antigenic determinants of ciguatoxin and may include monoclonal or polyclonal antibodies. Such antibodies can be prepared by conventional techniques which are known in the art. The animals used for the preparation of the antibodies are immunized with a ciguatoxin-containing fish extract (also referred to as "toxic fish extract") or a ciguatoxin analog.

Other assay procedures use "immunobeads," which comprise colored latex beads coated with antibody against ciguatoxin. Suitable immunobeads are made from blue-colored latex beads of about 0.3 to about 0.4 μm in diameter, such as those supplied by Seradyn, Inc., Particle Technology Division Ind., of Indianapolis, Ind. However, other-sized latex beads may be used.

Fish are screened by binding ciguatoxin, which may be present in the tissue of the fish, to a test support. Suitable supports may be bamboo sticks, which are coated with an organic-base solvent correction fluid such as LIQUID PAPER, supplied by Pentel of America, Ltd., Torrance, Calif., to form paddle supports, or membrane supports. Membrane supports comprise membrane material, such as that supplied by Millipore, of Bedford, Mass., under the name "MILLIPORE IMMOBILON-P MEMBRANE #IPVH," attached to a "dipstick." Polystyrene strips are suitable for use as dipsticks. The membranes are attached to the dipsticks by using an adhesive, such as "3M MEDICAL GRADE ADHESIVE #3044," or other suitable means of attachment.

After the support has been contacted with the fish tissue or extracts, it is contacted with the immunobeads. If ciguatoxin is present in the fish, the antibodies bind to the ciguatoxin on the support. Since the antibodies are also bound to the colored latex beads, the colored latex beads become bound to the ciguatoxin on the support. Therefore, a positive result, indicating the presence of ciguatoxin in the fish tissue, is observed by a change in color of the support due to colored latex beads being bound to the support.

When the antibody-horseradish peroxidase assay method is used, a positive result is observed by the accumulation of product from the enzyme assay.

In use, the assay reactions, described above, are compared to negative and positive controls. The negative controls are test supports which have not been exposed to ciguatoxins or their analogs.

CIGUATOXIN ASSAYS

Ciguatoxin is isolated by cutting an incision into the filet portion of a fish, near the head region. The LIQUID PAPER-coated end or membrane end of a "test" support is inserted into the incision and pushed up and down, to contact the fish tissue. The support is then air-dried and fixed quickly by dipping in absolute methanol for about 1 to about 3 seconds, and is again air-dried. The coated methanol-fixed end of the support is immersed into an immunobead suspension or other assay reagent. After 5 minutes' immersion in the immunobead suspension, the support is washed in phosphate-buffered saline, or other suitable wash solution, and examined.

If a distinct coloration of the support is observed, similar to that obtained with the positive control, after 5 minutes' immersion in the immunobead suspension, the test is considered positive, and the fish should not be eaten.

If, after 5 minutes' immersion in the immunobead suspension, the support has no color or very diffuse color, similar to that obtained with the negative control, the support is immersed in the immunobead suspension for an additional 5 minutes. If, after a total of 10 minutes, no color or very diffuse color of the support is observed, the result of the test is considered to be negative. In the case of a negative result, the same procedure, i.e., inserting a support into a fish and immersing the support in an immunobead suspension for up to 10 minutes, is repeated by inserting an additional support into a different area of the same fish. If the support is again negative after 10 minutes, the fish is considered safe to eat.

Intermediate readings, in which some coloration of at least one of the two supports used is observed after 10 minutes, or in which one support gives distinct coloration, indicate that the fish is probably contaminated and should not be eaten.

Negative control supports (supports which are identical to the paddle supports described above but which have not been exposed to ciguatoxins or their analogs) are subjected to the same treatment as described above for the test paddle supports. Similarly, a sample which gives a positive result (positive control) is also subjected to the same treatment as described for the test paddle supports. The negative and positive control supports are used to ensure that the reagents used in the assay are functioning correctly, and also for comparing with the test paddle supports to determine if a positive or a negative result has been obtained.

POSITIVE CONTROLS COMPRISING OKADAIC ACID

Assays for ciguatoxin ideally require the use of a positive control to determine if the reagents used in the assay are functioning correctly. Thus, when a negative result is obtained, it can be determined that the negative result is due to the lack of ciguatoxin contamination in the fish being tested, rather than due to a malfunction of the assay method. Also, the antibodies used in the assays need to be titered, to determine the useful range of antibody to be used in assay reactions. Such assays are important, since the use of too little antibody may cause the reaction to give a false negative result, and the use of too much antibody means that the assays are wasteful of this valuable reagent.

Previously, fish extracts had been used as the positive control for ciguatoxin assays and for titering antibodies and other assay reagents. However, these extracts vary in their composition, with respect to the ciguatoxins present in the extract and the concentration of the ciguatoxin present, and, therefore, also vary in their reactivity. Also, since the composition of the fish extract is unknown the use of fish extracts introduces a variable, into the assays for ciguatoxin contaminated fish, that can not be controlled. Therefore, fish ciguatoxin extracts exhibit variable reactivity and give results that are not reproducible or reliable.

Okadaic acid, which is commercially available from Sigma Chemical Co. of St. Louis, Mo., Catalog No. O-1506, has been found to mimic ciguatoxins in ciguatoxin assays. Compositions comprising okadaic acid have a known formulation and concentration and which give predictable and reproducible reactivity when assayed in ciguatoxin assays.

The reproducibility of the reactions obtained with okadaic acid allows assay parameters to be standardized so that assay kits or the like can be mass-produced. Okadaic acid is used as a means of quality control to ensure that kits produced are of a standard, acceptable quality and that the quality of the kits produced does not change over time.

For use in ciguatoxin assays, okadaic acid is mixed with a carrier. Carriers suitable for use in the present invention are carriers such as: fish extract obtained from either toxic or non-toxic fish and prepared as described below or by other suitable methods; oil/organic solvent mixtures; non-ionic detergent solutions; or fatty-acid solutions.

Positive controls are prepared by immersing a support, as described above, in an okadaic acid/carrier mixture. The positive control is then assayed as described above or by other suitable assay methods.

PREPARATION OF FISH EXTRACTS

Fish extracts, from either toxic or non-toxic frozen fish, are prepared by weighing out about 250 g of fish. The fish tissue may be autoclaved for about 10 minutes, if desired, to facilitate de-boning and to aid in the preparation of the fish extract. The bones are removed, and the tissue is homogenized in a blender at high speed for about 10 minutes. The homogenized tissue is diluted 50% w/v with acetone, and the mixture is blended for about another 5 minutes. The mixture is then centrifuged at about 2,000 rpm for about 15 minutes, at 4° C., to separate the phases. The upper, acetone phase is decanted and collected, and the acetone extraction procedure is repeated, on the residue/aqueous phase, three more times. The extract is stored at about −18° C. for about 10 to about 20 hrs. The solution is filtered in a cold Buchner funnel, and any residue is discarded. Acetone is removed from the non-volatile material by rotary evaporation.

Two volumes of methanol are added to the non-volatile material remaining after rotary evaporation, and the solution is mixed. The mixture is extracted three times with about a ¼ volume of hexane. The hexane phase is separated from the methanol-containing phase and discarded. The methanol is separated from the non-volatile material by rotary evaporation.

An approximately-equal volume of chloroform is added to the non-volatile material, and the mixture is shaken to extract the non-volatile material. The chloroform phase is then collected. The chloroform extraction is repeated two more times. The chloroform extracts are combined, and the chloroform is evaporated in a steam bath. The residue remaining after the chloroform is evaporated is crude fish extract.

Crude extract may be further purified by thin-layer chromatography (TLC) on silica gel TLC plates or by column chromatography.

The thin-layer chromatographic plate is developed with a chloroform/methanol mixture at a ratio of 8:2. The ciguatoxin fraction is recovered from the TLC plate, after the TLC plate has been run to separate the components of the crude extract, by scraping into a container the TLC medium from the section of the TLC plate containing the polyether fraction. The purified fish extract is then eluted from the collected TLC medium with chloroform:methanol in a ratio of 95:5. The eluate is evaporated to dryness and resuspended in about 5% Tween 60.

When column chromatography is used for the further purification of the crude extract, silicic acid, supplied by Mallicrodt, is used as the chromatography medium. Preferably, 100 mesh silicic acid is used, and it is activated at 100° C. for 1 hour, prior to use. The silicic acid is poured into a column of about 2 cm by about 5 cm, for use. The chromatographic medium is prepared by adding about a 1 cm layer of anhydrous $Na_2SO_4$ on top of the chromatographic medium in the column and equilibrating the chromatographic medium with chloroform. The crude extract is dissolved in chloroform to a concentration of about 40 mg/ml and applied to the chromatographic medium. The chromatographic medium is washed with about 20 ml of chloroform to elute triglycerides, fatty acids, cholesterol, and other non-polar compounds from the chromatographic medium. Ciguatoxins and other polyethers are eluted with a mixture of chloroform and methanol in a ratio of 95:5. The eluate is evaporated to dryness and resuspended in about 5% Tween 60.

CARRIERS SUITABLE FOR USE WITH OKADAIC ACID

When okadaic acid and fish-extract carriers are used as the positive control, supports, as described above, are immersed in solutions comprising about 0.1 µg/ml to about 0.8 µg/ml okadaic acid and about 2 to about 10 mg/ml fish extract. Concentrations above 0.8 µg/ml can be used; however, a reaction is obtained that is much stronger than the reaction which would be expected to be observed for a positive test support. Such a result could lead the user of the test to incorrectly determine, by comparison of a positive test support with the positive control, that the reaction obtained with the test strip was negative, rather than positive. Concentrations below about 0.1 µg/ml result in a reaction that is very weak and difficult to distinguish from the negative control.

The amount of fish extract used as carrier can be decreased as the amount of okadaic acid is increased. Preferably, a concentration of about 0.5 µg/ml okadaic acid with about 4 mg/ml of fish extract carrier is used, since this concentration simulates the expected results which would be obtained with a positive test support of about 25 mg/ml of ciguatoxin-containing fish extract. The minimum ciguatoxin assay result, which will cause toxicity to humans when the contaminated fish tissue is consumed, is considered to be equivalent to the assay results obtained with about 25 mg/ml ciguatoxin-containing fish extract. However, other concentrations of okadaic acid and fish extract carriers can be used, and can be varied to suit the needs of the assay being performed.

Oil/organic solvent mixtures suitable for use as carrier in the present invention are mixtures such as olive oil in butanol, safflower oil in butanol, olive oil in hexane, safflower oil in hexane, soybean oil in hexane, and jojoba oil in hexane, although other mixtures of oil and organic solvents can also be used. Preferably, the ratio of oil:organic solvent is about 1:10. About 0.1 to about 0.8 µg/ml okadaic acid is added to the oil/organic solvent mixtures. Most preferably, about 0.5 μg/ml okadaic acid is used, which gives a result similar to that obtained with 25 mg/ml of toxic fish extract.

Preparations of oil alone can be used as a carrier for the okadaic acid; however, such preparations leave an oily film on the support. The incorporation of an organic solvent into the preparation reduces the amount of oil left on the support and aids in the drying of the support after impregnation with the okadaic acid composition.

Non-ionic, detergent solutions suitable for use as carrier in the present invention are aqueous solutions prepared with detergents such as the polyoxyethylenesorbitans (Tween 20, Tween 40, Tween 60, Tween 80 and Tween 85). Preferably, about 5%, by volume, non-ionic detergent is used. About 0.1 to about 0.8 μg/ml okadaic acid is added to the detergent solutions. Most preferably, about 0.5 μg/ml okadaic acid is used, which gives a result similar to that obtained with 25 mg/ml of toxic fish extract.

Fatty-acid solutions suitable for use as carrier in the present invention include fatty acids such as lauric acid, linoleic acid, myristic acid, palmitic acid, stearic acid, oleic acid, and mixtures thereof. Preferably, about 5%, by volume, aqueous fatty-acid solutions are used. About 0.1 to about 0.8 μg/ml okadaic acid is added to the fatty-acid solutions. Most preferably, about 0.5 μg/ml okadaic acid is used, which gives a result similar to that obtained with 25 mg/ml of toxic fish extract.

ASSAY METHODS WITH OKADAIC ACID

Determination of the sensitivity and specificity of antibody or immunobead preparations can be conducted by coating a number of different supports with a solution containing either 0.2, 0.3, 0.4, 0.5, 0.6, 0.7, 0.8 μg/ml of okadaic acid, or other suitable concentration ranges in the presence of carrier. When the okadaic acid-supports are exposed to the immunobeads, the immunobead antibodies bind to the okadaic acid, resulting in the presence of a blue color on the support which will not be washed off by rinsing in a wash solution such as phosphate-buffered saline. The intensity of the blue color increases with increasing concentrations of okadaic acid. It is preferred that the immunobeads bound to the support result in a distinct blue color, with supports coated with at least about 0.4 to about 0.6 μg/ml okadaic acid. Most preferably, the distinct blue color will be developed with supports coated with at least about 0.5 μg/ml of okadaic acid. If the immunobeads do not result in a distinct blue color with at least 0.6 μg/ml okadaic acid, the immunobeads may not be sufficiently sensitive to reliably detect contaminated fish. If the immunobeads react with less than about 0.4 μg/ml okadaic acid to give a distinct blue color, an excessive amount of antibody has been bound to the latex bead, and preparation of immunobeads with such high amounts of antibodies is wasteful of this valuable reagent. Similar assays can be conducted with antibodies coupled to enzymes or other assay methods.

The intensity of the distinct blue color of the positive reaction is chosen so that the color of a positive reaction (for example, the reaction obtained with a positive control) is clearly distinguished from a negative reaction (for example, the reaction obtained with a negative control) when the positive and negative reactions are compared side-by-side.

USE OF OKADAIC ACID IN FIELD KITS

The composition of the present invention is also appropriate for use in field kits for the detection of ciguatoxin contamination in fish. Field kits are particularly useful for sportsfisherman, who can test the fish they catch. The okadaic acid positive control is useful in such field kits to ensure that the user of the field kit can evaluate the results obtained with the test support and can distinguish between a positive and a negative assay result.

Such field kits comprise:

negative controls, which are supports which have not been exposed to ciguatoxin-containing fish extract, ciguatoxin analogs, or okadaic acid;

positive controls, which are supports that have been exposed to compositions comprising okadaic acid;

test supports, which are supports which are to be contacted with fish extracts or the flesh of fish suspected of being contaminated with ciguatoxin;

a fixation reagent, which is preferably absolute methanol;

an assay reagent, such as an immunobead suspension; and a wash solution, such as phosphate-buffered saline.

The supports suitable for practice of this invention are bamboo, with one end coated with correction fluid, membranes attached to a dipstick, or other suitable supports.

EXAMPLE 1

Assay of Toxic Fish Extract Using an Immunobead Assay

Membrane supports were exposed to various concentrations of a fish extract derived from toxic Po'ou fish (Wrasse fish). The membrane portion of a membrane support was inserted into solutions which contained either 1, 5, 10, or 25 mg/ml of fish extract. The membrane supports were removed and air-dried for about 5 minutes or until the membranes were dry.

The membrane supports were fixed by immersing the membranes in absolute methanol for about 1 second. The membrane supports were again air-dried for about 5 minutes. Each of the membrane supports was then immersed in 0.5 ml of an immunobead suspension and allowed to remain in the immunobead suspension, undisturbed, for about 5 minutes. After 5 minutes, the membrane supports were removed from the immunobead suspension and washed three times with phosphate-buffered saline. Any excess liquid was removed by blotting the support with a paper towel.

The color developed on the test membrane supports was evaluated and the results scored.

The results of the assays conducted with various concentrations of toxic fish extract are summarized in Table I. Also included, for comparison, are similar assays conducted with paddle supports. The paddle support assays were performed as described above for the membrane supports, except paddle supports were used in place of the membrane supports.

TABLE I

| Toxic Fish Extract[b] | Paddle Support | Membrane Support |
|---|---|---|
| 1 mg/ml | 10/10[a] | 4/4 |
| 5 mg/ml | 10/10 | 4/4 |
| 10 mg/ml | 9/10 | 15/15 |
| 25 mg/ml | 7/7 | 14/14 |

[a]Number positive results/number of supports assayed.
[b]Color intensity increased with increased concentration of extract.

The results indicate that membrane and paddle supports are sensitive to and effective in the detection of toxin.

EXAMPLE 2

Assays of Mixtures of Toxic Fish Extract and Okadaic Acid

The assay procedure described in Example 1 was repeated, except that 0.2 μg/ml of okadaic acid (OA) was added to each of the toxic fish extract solutions.

The color developed on the test membrane and paddle supports was evaluated and the results scored. The results of the assays are summarized in Table II.

TABLE II

| Toxic Fish Extract Plus Okadaic Acid[b] | Paddle Support | Membrane Support |
|---|---|---|
| 1 mg/ml + 0.2 μg OA | 4/4[a] | 4/4 |
| 5 mg/ml + 0.2 μg OA | 4/4 | 4/4 |
| 10 mg/ml + 0.2 μg OA | 4/4 | 4/4 |

[a]Number positive results/number of supports assayed.
[b]Color intensity increased with increased concentration of extract.
[c]Color intensity of 10 mg toxic extract/ml + 0.2 μg OA was equal to 25 mg/ml toxic fish extract.

The results indicate that okadaic acid does not interfere with the test and that okadaic acid is also detected by the assay procedures.

EXAMPLE 3

Assay of Okadaic Acid-Impregnated Fish

The assay procedure described in Example 1 was repeated, except that membrane supports were exposed to toxic or non-toxic barracuda flesh or non-toxic barracuda flesh which had been impregnated with 0.1, 0.2, 0.3 or 0.4 μg okadaic acid and blended with the tissue. The test supports were inserted into the artificially contaminated flesh of the fish.

The color present on the test membrane supports was evaluated and the results scored. The results of the assays are summarized in Table III.

TABLE III

| Sample | Membrane Support |
|---|---|
| Toxic fish (cooked)[a] | 6/6[b] |
| Non-toxic fish (uncooked) | 0/3 |
| Non-toxic fish + 0.1 μg OA | 7/7 |
| Non-toxic fish + 0.2 μg OA | 7/7 |
| Non-toxic fish + 0.3 μg OA | 7/7 |
| Non-toxic fish + 0.4 μg OA | 16/16 |

[a]Sample implicated in a ciguatera poisoning outbreak.
[b]Number positive results/number of supports assayed.
[c]Color intensity increased with increased concentration of okadaic acid.

The results indicate that okadaic acid does not interfere with the assay method and that okadaic acid is detected by the assay procedures.

EXAMPLE 4

Assay of Toxic Fish Extracts and Okadaic Acid Mixture

The assay procedure described in Example 1 was repeated, except that membrane supports were exposed to 4 mg/ml toxic fish extract to which either 0.1, 0.2, 0.3, 0.4, or 0.5 μg/ml of okadaic acid had been added.

The color developed on the test membrane supports was evaluated and the results scored to determine the usefulness of okadaic acids as a positive control. The results of the assays are summarized in Table IV.

TABLE IV

| Sample[b] | Membrane Support |
|---|---|
| 4 mg/ml toxic fish extract + 0.1 μg OA | 4/4[a] |
| 4 mg/ml toxic fish extract + 0.2 μg OA | 4/4 |
| 4 mg/ml toxic fish extract + 0.3 μg OA | 4/4 |
| 4 mg/ml toxic fish extract + 0.4 μg OA | 4/4 |
| 4 mg/ml toxic fish extract + 0.5 μg OA | 15/15 |

[a]Number positive results/number of supports assayed.
[b]Color intensity increased with increased concentration of extract.

The results indicate that increasing okadaic acid results in a corresponding increase in the intensity of the assay result obtained.

The above description of exemplary embodiments for assays using okadaic acid are for illustrative purposes. Because of variations which will be apparent to those skilled in the art, the present invention is not intended to be limited to the particular embodiments described above. Also, the invention disclosed may be practiced in the absence of any element which is not specifically disclosed in the specification. The scope of the invention is defined by the following claims.

What is claimed is:

1. A kit for detecting the presence of ciguatoxin or related polyether marine toxins in fish, comprising positive control reagents which react reproducibly with antibodies against ciguatoxins or related polyether marine toxins wherein the positive control reagents comprise:

okadaic acid; and
a carrier, selected from the group consisting of toxic fish extract, non-toxic fish extract, oils, oil/organic solvent mixtures, fatty-acid solutions, and nonionic detergent solutions.

2. A kit as recited in claim 1 further comprising:
supports for binding toxin;
negative control supports;
absolute methanol for fixing toxin to the support;
an assay reagent for assaying toxin or okadaic acid bound to the fixed support: and
a buffer solution for washing the fixed toxin-bound supports after they have been contacted with the assay reagent.

3. The kit as recited in claim 1, wherein the assay reagent comprises immunobeads.

4. The kit as recited in claim 1, wherein the positive control reagents are supports impregnated with a composition comprising about 0.1 to about 0.8 μg/ml okadaic acid.

5. The kit as recited in claim 1, wherein the oil carrier is selected from the group consisting of soybean oil, jojoba oil, olive oil, safflower oil, or mixtures thereof.

6. The kit as recited in claim 1, wherein the organic solvent of the oil/organic solvent mixture is selected from the group consisting of hexane, butanol, and mixtures thereof.

7. The kit as recited in claim 6, wherein the ratio of oil:organic solvent in the oil/organic solvent mixture is about 1:10.

8. The kit as recited in claim 1, wherein the fatty-acid carrier is selected from the group consisting of lauric acid, linoleic acid, myristic acid, palmitic acid, stearic acid, oleic acid, and mixtures thereof.

9. The kit as recited in claim 8, wherein the fatty acids are present at about 5% by volume.

10. The kit as recited in claim 1, wherein the non-ionic detergent carrier is selected from the group consisting of the polyoxyethylenesorbitan detergents and mixtures thereof.

11. The kit as recited in claim 10, wherein the non-ionic detergent is present at about 5% by volume.

12. The kit as recited in claim 1, wherein the positive control reagents are so constituted as to result in a reaction, when assayed, equal to the intensity obtained with about 25 mg/ml toxic fish extract.

13. A method of preparing a positive control reagent for use in assays for the detection of ciguatoxins and related polyether marine toxins, comprising:
mixing okadaic acid with a carrier, selected from the group consisting of toxic fish extract, non-toxic fish extract, oils, oil/organic solvent mixtures, fatty-acid solutions, and non-ionic detergent solutions wherein the okadaic acid/carrier mixture reacts reproducibly with antibodies against ciguatoxin or related polyether marine toxins; and
applying the okadaic acid/carrier mixture to a support.

14. The method as recited in claim 13, wherein the okadaic acid is dissolved to a concentration of about 0.1 $\mu$g/ml to about 0.8 $\mu$g/ml.

15. The method as recited in claim 13, wherein the carrier is selected from the group consisting of fish extract, oils, oil/organic solvent mixtures, fatty-acid solutions, and non-ionic detergent solutions.

16. The method as recited in claim 15, wherein the oil is selected from the group consisting of soybean oil, jojoba oil, olive oil, safflower oil, or mixtures thereof.

17. The method as recited in claim 15, wherein the solvent of the oil/organic solvent mixture is selected from the group consisting of hexane and butanol.

18. The method as recited in claim 17, wherein the ratio of oil:organic solvent in the oil/organic solvent mixture is about 1:10.

19. The method as recited in claim 15, wherein the fatty acid is selected from the group consisting of lauric acid, linoleic acid, myristic acid, palmitic acid, stearic acid, oleic acid, and mixtures thereof.

20. The method as recited in claim 19, wherein the fatty acid is present at about 5% by volume.

21. The method as recited in claim 15, wherein the non-ionic detergent is selected from the group consisting of the polyoxyethylenesorbitan detergents and mixtures thereof.

22. The method as recited in claim 21, wherein the non-ionic detergent is present at about 5% by volume.

23. A method for performing a positive control assay in the detection of ciguatoxins and related polyether marine toxins comprising:
mixing okadaic acid with a carrier;
applying the okadaic acid/carrier mixture to a support;
fixing the okadaic acid/carrier mixture to the support;
contacting the okadaic acid/carrier mixture, bound to the support, to an antibody against ciguatoxin;
washing any unbound antibody from the support; and
quantitating the amount of antibody bound to the support.

24. A positive control reagent comprising:
okadaic acid; and
a carrier, selected from the group consisting of toxic fish extract, non-toxic fish extract, oils, oil/organic solvent mixtures, fatty-acid solutions, and non-ionic detergent solutions, wherein the okadaic acid/carrier mixture reacts reproducibly with antibodies against ciguatoxin or related polyether marine toxins.

25. A positive control reagent as recited in claim 24, wherein the okadaic acid is present at about 0.1 $\mu$g/ml to about 0.8 $\mu$g/ml okadaic acid.

26. A positive control reagent as recited in claim 24, wherein the oil is selected from the group consisting of soybean oil, jojoba oil, olive oil, safflower oil, or mixtures thereof.

27. A positive control reagent as recited in claim 24, wherein the organic solvent of the oil/organic solvent mixture is selected from the group consisting of hexane, butanol, or mixtures thereof.

28. A positive control reagent as recited in claim 24, wherein the ratio of oil:organic solvent in the oil/organic solvent mixture is about 1:10.

29. A positive control reagent as recited in claim 24, wherein the fatty acid is selected from the group consisting of lauric acid, linoleic acid, myristic acid, palmitic acid, stearic acid, oleic acid, and mixtures thereof.

30. A positive control reagent as recited in claim 29, wherein the aqueous fatty acid mixture is present at about 5% by volume.

31. A positive control reagent as recited in claim 24, wherein the non-ionic detergent is selected from the group consisting of the polyoxyethylenesorbitan detergents and mixtures thereof.

32. A positive control reagent as recited in claim 31, wherein the non-ionic detergent is present at about 5% by volume.

33. The positive control reagent as recited in claim 24, wherein the okadaic acid composition results in a reaction, when assayed, equal to the intensity obtained with assays of about 25 mg/ml toxic fish extract.

* * * * *

UNITED STATES PATENT AND TRADEMARK OFFICE
CERTIFICATE OF CORRECTION

PATENT NO. : 5,206,141
DATED : April 27, 1993
INVENTOR(S) : Douglas L. Park

It is certified that error appears in the above-indentified patent and that said Letters Patent is hereby corrected as shown below:

Column 3, line 34, change "Particle Technology Division Ind." to -- Particle Technology Division Inc. --.

Column 4, lines 12,19,21, change "minutes'" to -- minutes -- (all occurrences).

Column 8, line 15, change "sportsfisherman" to -- sport fishermen --.

Column 10, line 58, change "claim 1" to -- claim 2 --.

Signed and Sealed this

Twenty-first Day of June, 1994

Attest:

BRUCE LEHMAN

Attesting Officer     Commissioner of Patents and Trademarks